(12) United States Patent
Smith et al.

(10) Patent No.: US 10,345,245 B2
(45) Date of Patent: *Jul. 9, 2019

(54) LUMINESCENCE MEASUREMENTS IN DIAMOND

(71) Applicant: De Beers UK Ltd, London, Greater London (GB)

(72) Inventors: James Gordon Charters Smith, Buckinghamshire (GB); Colin McGuinness, Berkshire (GB); David Fisher, Berkshire (GB)

(73) Assignee: De Beers UK Ltd, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/107,503

(22) Filed: Aug. 21, 2018

(65) Prior Publication Data

US 2019/0003980 A1 Jan. 3, 2019

Related U.S. Application Data

(63) Continuation of application No. 15/739,740, filed as application No. PCT/GB2016/051927 on Jun. 28, 2016, now Pat. No. 10,082,469.

(30) Foreign Application Priority Data

Jun. 30, 2015 (GB) .................................. 1511461.4

(51) Int. Cl.
*G01N 21/87* (2006.01)
*G01N 21/64* (2006.01)

(52) U.S. Cl.
CPC ............. *G01N 21/87* (2013.01); *G01N 21/64* (2013.01)

(58) Field of Classification Search
CPC .............................. G01N 21/87; G01N 21/64
USPC .......................................................... 356/30
See application file for complete search history.

(56) References Cited

U.S. PATENT DOCUMENTS

| | | | |
|---|---|---|---|
| 5,801,819 A | 9/1998 | Spear |
| 5,883,389 A | 3/1999 | Spear |
| 6,014,208 A | 1/2000 | Welbourn et al. |
| 2006/0062446 A1 | 3/2006 | Porat |

FOREIGN PATENT DOCUMENTS

| | | |
|---|---|---|
| EP | 0341092 A2 | 11/1989 |
| EP | 0341093 A2 | 11/1989 |
| EP | 0345949 A2 | 12/1989 |
| GB | 1384813 A | 2/1975 |
| GB | 2336901 A | 11/1999 |
| GB | 2 516 297 A | 1/2015 |

(Continued)

OTHER PUBLICATIONS

International Search Report for corresponding International Application No. PCT/GB2016/051927 dated Oct. 10, 2016.

(Continued)

*Primary Examiner* — Hina F Ayub
(74) *Attorney, Agent, or Firm* — Renner Otto Boisselle & Sklar, LLP

(57) ABSTRACT

A method of and an apparatus for providing an indicator for a diamond as to whether it is natural by testing for the presence or absence of one or more specific markers in the luminescence properties of the diamond, These markers are characterized by luminescence decay time and luminescence wavelength.

19 Claims, 12 Drawing Sheets

(56) References Cited

FOREIGN PATENT DOCUMENTS

WO      WO 99/57544 A1    11/1999

OTHER PUBLICATIONS

International Preliminary Report on Patentability for corresponding International Application No. PCT/GB2016/051927 dated Sep. 22, 2017.
Search Report for corresponding United Kingdom application No. 1511461.4, dated Nov. 27, 2015.
Takiyama K etal: "Photoluminescence and decay kinetics of indirect free excitons in diamonds under the near-resonant laser excitation", Solid State Communications. Pergamon. GB. vol. 99, No. 11, Sep. 1, 1996 (Sep. 1, 1996). pp. 793-797. XP002111815. ISSN: 0038-1098.
Lindblom, J.; Hölsä, J.; Papunen, H.; Häkkänen, H.; Mutanen, J.; "Differentiation of natural and synthetic gem-quality diamonds by luminescence properties"; Elsevier B.V.; 0925-3467; Feb. 24, 2003.
American Mineralogist 2005 vol. 90; No. 2/3, pp. 428-440; Lindblom, J. Hölsä, J.; Papunen, H. Häkkänen, H.; Luminescence Study of Defects in Synthetic As-Grown and HPHT Diamonds Compared to Natural Diamonds Mineralogical Society of America; 0845.000000.
Tarasenko et al., Photoluminescence and optical transmission of diamond and its imitators, Proc. of SPIE vol. 7751 77511F-1, 2010.
Lipatov et al., Photoluminescence and optical transmission of diamond and its imitators, Journal of Luminescence 130, pp. 2106-2112, Jun. 16, 2010.
Lipatov et al., Identification of Diamond and its Imitators with Using Excilamp, Modification of Material Properties, pp. 380-382, May 1, 2014.

LUMINESCENCE MEASUREMENTS IN DIAMOND

TECHNICAL FIELD

The present invention relates to a method and apparatus for the measurement of luminescence properties in diamonds. In particular, although not exclusively, the invention relates to the application of such measurement to the detection as to whether a diamond is natural.

BACKGROUND

Synthetic or man-made diamonds, manufactured by HPHT (high pressure high temperature), CVD (chemical vapour deposition) or other industrial, non-geological processes, have a wide variety of industrial applications, but currently form only a small percentage of the gemstone industry. Being man-made, they do not attract the high values associated with natural diamonds of similar colour and quality and it is clearly desirable from a consumer perspective to provide reliable means of identifying and separating synthetic diamonds from natural ones.

Treated diamonds are natural diamonds which have been artificially enhanced to improve their physical characteristics, usually in terms of their colour or quality. Colour changes can be induced via treatments such as the application of coatings, irradiation and heating. Heating at high temperatures can lead to the conversion of diamond to graphite and this is avoided by applying a stabilising pressure during heating, so called High Pressure High Temperature (HPHT) treatment. Quality can be improved by the application of treatments such as the filling of cracks to reduce their visibility and the removal of inclusions using laser drilling. Diamonds treated in such ways are also considered to be of lower value than the equivalent diamond that has not been subjected to treatment and detection techniques for such treatments are an essential part of ensuring that the purchaser of a diamond can make a fully informed decision about their purchase.

The task of identifying the origin of a gemstone typically falls to a diamond appraiser, grader or gemmologist in the course of preparing a grading certificate or appraisal. The origin of a diamond is a key factor in its market value and is of paramount importance to the gemmologist. There are numerous characteristics that can be used to distinguish between the diamond from nature and one produced from an industrial process (which may be called a synthetic) but the inherent variability in the natural diamond and of the synthetic processes makes such a task difficult and onerous.

One characteristic that has proven to be of utility is the emission of luminescence when a diamond is illuminated (or excited) by a source of energy, most commonly but not exclusively, electromagnetic radiation. A gemmologist would normally have an ultraviolet lamp, perhaps emitting radiation with a wavelength of 365 nm or 254 nm (nanometers), these being common lines in the emission of the low pressure mercury lamp, and might observe what would be called fluorescence. Fluorescence is a type of luminescence characterised as only being produced when the ultraviolet excitation is on. Phosphorescence, which may also be observed, is a type of luminescence that remains but decays away once the excitation is removed. Through interpretation of any such luminescence present, taking into account their observable temporal characteristics, colours and spatial distribution inferences on the task at hand may be drawn as is known in the art.

The DiamondView® as disclosed in U.S. Pat. No. 5,883,389 allows a more sophisticated observation to be made. In particular it offers a source of shorter wave ultraviolet radiation (characterised in having a wavelengths of less than 225 nm) corresponding to the primary absorption edge and only penetrating a very small amount (about 1 µm) into the surface of the diamond so that one could consider that any observed luminescence is produced at the surface. The instrument as disclosed may also incorporate a sensitive camera so that images may be recorded of the observed luminescence and phosphorescence but this is not an essential feature.

A competent gemmologist will know that the terms fluorescence and phosphorescence, while convenient, are merely a loose way of describing the temporal characteristics of luminescence. They describe emissions that decay away quickly or slowly on a time scale of human observation. Not surprisingly the temporal characteristics of luminescence are far more complex. It is known for example that, if subjected to a hypothetically very short pulse of excitation, luminescence may be observed to decay on time scales from picoseconds to tens of seconds. There are also multiple possible decay laws, such as an exponential decay or a power law decay, depending on the kinetics of the underlying radiative and competing non-radiative processes. Furthermore, a sample may show a combination of emission colours or wavelengths and temporal characteristics in each of a plurality of locations.

Said gemmologist might also know that a fuller understanding of said temporal, spatial and spectral characteristics would be advantageous to the task at hand, but lacks a convenient apparatus and method to perform the required observations in a practical manner in a reasonable time and at economic cost beyond what can in essence be performed by eye.

SUMMARY

In accordance with one aspect of the present invention there is provided a method of providing an indicator for a diamond as to whether it is natural and/or what type it is by testing for the presence or absence of one or more specific markers in the luminescence properties of the diamond, said markers characterised by luminescence decay time and luminescence wavelength.

The method may comprise irradiating the diamond with at least one excitation pulse of electromagnetic radiation, and during and/or following the excitation pulse, detecting light emitted by the diamond in at least one time window having a predetermined time relationship relative to the excitation pulse so as to obtain luminescence data. The or each time window is chosen to include luminescence having a decay time characteristic of one or more of the markers. The luminescence data is analysed in order to establish the presence or absence of the one or more markers.

The decay time may be defined as the time taken for the number of excited molecules to decay to 1/e or 36.8%. Thus luminescence emitted in specific time windows during or after the excitation pulse can be used to identify whether predetermined markers are present.

The radiation of the excitation pulse may be in the ultraviolet spectrum, and optionally 225 nm or less.

The diamond may be irradiated with multiple excitation pulses. Luminescence data may then be obtained from at least one time window associated with each excitation pulse, each time window being closed before the start of the next excitation pulse.

Where multiple excitation pulses are used, the luminescence data associated with all of the pulses may be combined. This combination may be in the form of averaging, so that the luminescence data obtained in a specific time window associated with each excitation pulse is averaged over all of the pulses so as to produce an averaged image or spectrum for the light emitted in that time window. This can improve signal to noise of a spectral line emitted in a very narrow time window, for example, making it possible to isolate markers with very specific wavelength and decay characteristics. Similarly, an averaged image can display features from a particular decay time that would otherwise be invisible to a user.

Alternatively (or an addition) a different form of combination of luminescence data may be possible if individual images are obtained from each time window. This combination of the luminescence data is achieved by displaying images for corresponding time windows from all excitation pulses sequentially to the user, optionally in the form of a video. This enables the user to pick out features by identifying consistent features between images.

A light source for the excitation pulses may be synchronised with a light detector. An individual time window may be opened after the associated excitation pulse has ended, so that the luminescence data comprises phosphorescence data. Alternatively or in addition, a time window may be opened at the same time or very shortly after the start of the associated excitation pulse and closing said time window before or at the same time as the associated pulse ends, so that the luminescence data comprises fluorescence data.

One of the markers may be a blue fast phosphorescence marker comprising luminescence in a wavelength band peaking at about 450 nm and a decay time of less than about 80 ms. Testing for this may involve testing, in a time window opening at or after the end of the excitation pulse and ending about 80 milliseconds after the end of the associated excitation pulse, for a luminescence band peaking at about 450 nm. The presence of the blue fast phosphorescence marker may be an indicator that the diamond is a natural type IIa or Ia diamond.

One of the markers may be a turquoise slow phosphorescence marker comprising luminescence having a wavelength peaking at about 480 nm and a decay time greater than 80 milliseconds. Testing for this may comprise testing, in a time window opening about 80 milliseconds after the end of the associated excitation pulse, for a luminescence band centered around 480 nm. The time window may close about 500 ms after the end of the associated excitation pulse, especially if multiple excitation pulses are used. The presence of the turquoise slow phosphorescence marker may be an indicator that the diamond is a type IIb diamond.

One of the markers may be a green slow phosphorescence marker comprising luminescence having a wavelength between about 530 nm and about 550 nm and a decay time greater than 80 milliseconds. Testing for this marker may involve testing, in a time window opening about after the end of the associated excitation pulse, for a luminescence band between about 530 nm and about 550 nm. Again, the time window may optionally close about 500 ms after the end of the associated excitation pulse. The presence of the green slow phosphorescence marker may be an indicator that the diamond should be referred for further testing.

One of the markers may be an "absence" marker where negligible luminescence is detected after the excitation pulse has ended. The presence of such a marker is an indicator that the diamond should be referred for further testing.

One of the markers may be an orange long lived fluorescence marker comprising luminescence having a wavelength between about 535 nm and about 600 nm and a decay time less than 1 millisecond. The presence of the orange long lived fluorescence marker may be an indicator that the diamond should be referred for further testing.

One of the markers may be a red phosphorescence marker comprising luminescence having a wavelength between about 575 nm and about 690 nm and a decay time greater than 1 millisecond. The presence of the red phosphorescence marker may be an indicator that the diamond should be referred for further testing.

One of the markers may be a weak green fluorescence marker having a wavelength of about 510 nm. Testing for the weak green fluorescence marker may comprise testing in the time window synchronised with the excitation pulse. The presence of the weak green fluorescence marker may be an indicator that the diamond should be referred for further testing.

In accordance with another aspect of the present invention there is provided an apparatus for providing an indicator as to whether a diamond is natural and/or the type of the diamond by measuring luminescence properties of the diamond. The apparatus comprises a source of electromagnetic radiation, a light detection device for capturing visible light emitted by the diamond, and a control system. The control system is configured to synchronise the source and light detection device, to cause the source to irradiate the diamond with at least one excitation pulse of electromagnetic radiation, and to cause the light detection device to capture visible light emitted by the diamond during at least one time window having a predetermined time relationship relative to the excitation pulse so as to obtain luminescence data. The time window (or each time window if there is more than one) is chosen to encompass one or more specific markers in the luminescence properties of the diamond. The markers are characterised by luminescence decay time and luminescence wavelength and provide an indicator of the type of diamond and/or whether the diamond is natural.

The control system may be configured to cause the source to irradiate the diamond repeatedly with a series of excitation pulses. Where this is the case, the at least one time window is associated with each excitation pulse and is configured to close before the start of a subsequent excitation pulse.

The apparatus may comprise a processor to analyse the luminescence data associated with the or each pulse to determine whether a marker is present. The processor may be configured to combine luminescence data associated with all of the pulses. The combination may be by averaging luminescence data acquired over many pulses, and/or may involve obtaining an image from the luminescence data for each time window associated with each excitation pulse and displaying the images in sequence via a display device.

The control system may be configured to enable one or more of the following to be operator controllable: time window start time relative to excitation pulse start or end, length of time window, number of excitation pulses, frequency of excitation pulses. The control system may also be configured to allow a user to trigger a single excitation pulse (and associated luminescence data capture) or short set of excitation pulses.

DETAILED DESCRIPTION

Figure 1:
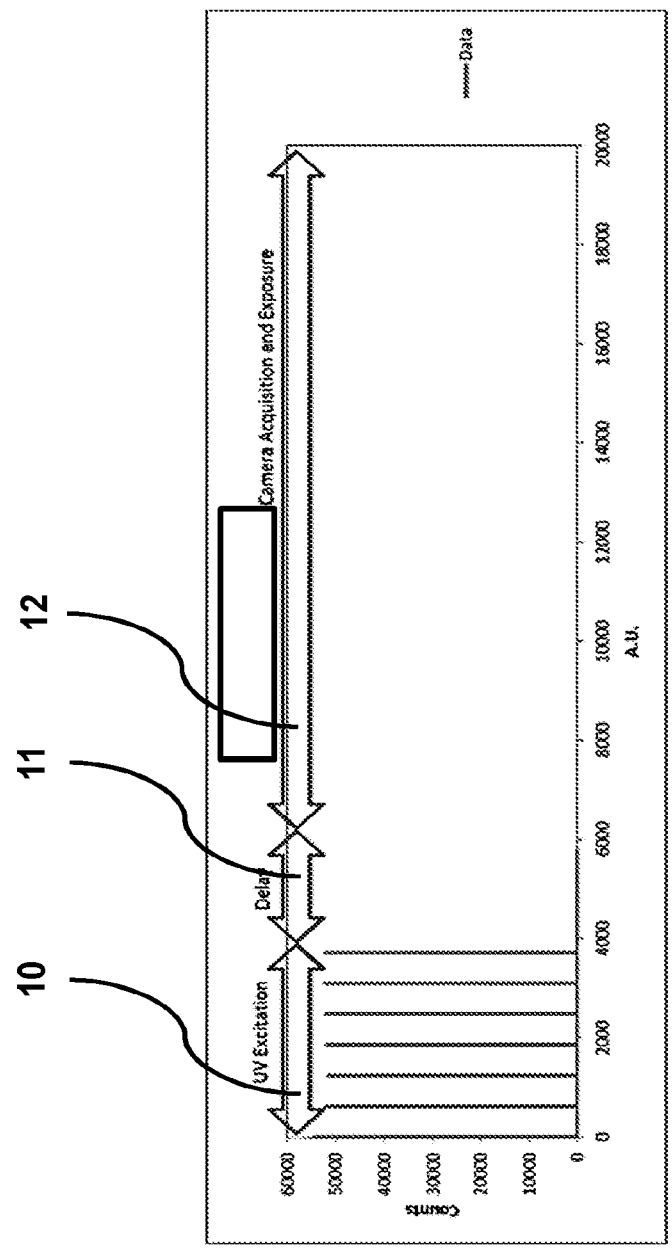
FIG. 1 is a graphical representation of a known method of long-lived phosphorescence measurement.

The basic crystal structure and chemical composition of synthetic and treated diamonds are the same as those of natural untreated diamond and therefore identification cannot be based upon relatively simple materials fingerprinting techniques (e.g. simplified applications of Raman spectroscopy and FTIR absorption). Detection is usually dependent on subtle differences in the atomic impurity centres that are present in the diamond and their spatial distributions.

The spatial distribution of atomic impurities is of particular importance when comparing natural and synthetic diamonds. Theoretical predictions indicate that the equilibrium growth mode of diamond is octahedral and many natural diamonds grow very near to equilibrium conditions and show octahedral growth, although there are relatively rare examples of diamonds that deviate from this. Synthetic diamonds are grown well away from equilibrium conditions and in an environment that can induce changes in the surfaces of the growing diamond that result in the presence of crystal surfaces not encountered in natural diamond. HPHT synthetics do show octahedral faces but in combination with one or more other growth faces (typically cubic and dodecahedral). Non-octahedral growth surfaces are also observed for CVD synthetics and additionally they generally exhibit pronounced steps on the growing surface.

These different growth modes in synthetics are evident in the shape of the final crystal, but also influence the distribution of impurities found throughout the resultant crystal because, during the course of growth, surfaces with different crystallographic orientations will take up impurities at different rates. These differences obviously persist when polished gemstones are manufactured, unlike the final crystal surfaces. This can result in large scale differences in impurity levels between regions corresponding to growth on a particular surface (growth sectors) in HPHT and CVD synthetics and smaller scale variations associated with step-flow growth in CVD synthetics due to differences between the orientations of risers and terraces. These differences in impurity concentrations will result in characteristic patterns when the mapped using a suitable technique and luminescence provides a very sensitive means of producing images of these distributions. It can also be the case that the uptake of a particular atomic impurity can be so low on most surfaces that it effectively only incorporates in one growth sector (e.g. nickel or cobalt incorporation in {111} growth sectors of HPHT synthetics).

Detection of these impurity distributions using luminescence has a number of benefits. The technique is sensitive to very low concentrations of impurities and changes in luminescence intensity can reveal very subtle variations in the concentration of the impurity involved. In natural diamonds, very small variations in the concentrations of impurities incorporated during the growth of the diamond can be imaged. The observed intensity can also be influenced by the presence of other impurities in close proximity to the luminescing impurity potentially providing an additional means of detecting differences between natural and synthetic diamonds. The interaction between impurity centres can also have a significant effect on the luminescence decay lifetime observed, with different impurities and the relative separation both influencing the degree of change in the measured lifetime.

Luminescence features are not exclusively confined to those generated due to impurity uptake differences during the course of growth. In natural diamonds, impurity centres can be modified as the diamond resides in the earth's mantle at elevated temperatures for long periods of time, although migration over significant distances is not usually observed. This will often result in a change in the colour of the observed luminescence. Defects in the crystal structure can also be generated as a consequence of the diamond being deformed in the earth's mantle. These defects can also show luminescence and have an influence on the characteristics of the luminescence emitted by other impurity centres.

Fluorescence colour and pattern can be utilised to determine whether the growth-related features are characteristic of synthetic or natural diamond. Long-lived phosphorescence can also be used to provide an indication as to whether a diamond is natural or synthetic, being rare in natural diamond and more common in synthetic diamond. Whilst long-lived phosphorescence does not provide a definitive means of identification in isolation, it can be used in combination with other observations to distinguish between synthetic and natural diamonds.

FIG. 1 is a graphical representation of a known method of phosphorescence measurement, in which a single measurement 12 is taken after removal of the UV source. A diamond sample is illuminated by a series of pulses 10 of UV light. After a delay 11, an image capture device obtains a single image 12 of the sample. The image capture device and UV source are not synchronised in any way. This method therefore captures only relatively long-lived phosphorescence and is generally used in addition to observation of the fluorescence colour and patterns produced by UV excitation of the sample surface.

Long-lived phosphorescence, which may persist for several seconds or more, is commonly occurring in synthetic diamond but is much rarer in natural diamond. An exception to this is natural Type IIb diamonds, which contain significant boron impurities. Type IIb diamonds account for perhaps only 0.1% of all natural diamonds so are fairly uncommon. The presence of relatively long-lived phosphorescence is therefore a known method of distinguishing a large proportion of synthetic diamonds from the vast majority of natural diamonds.

Some synthetic diamonds grown by CVD (chemical vapour deposition) do not exhibit the type of long-lived phosphorescence described above. Detection of long-lived phosphorescence in isolation could not be used to distinguish these from natural diamonds and other methods would be employed to definitively identify these synthetics.

It has been discovered that it is possible to distinguish between natural and synthetic diamond through measurement of much shorter-lived and weaker phosphorescence. This type of phosphorescence occurs for less than 100 milliseconds after removal of the UV source and therefore cannot be measured using the known method described above.

In order to measure this rapid phosphorescence, the image capture device and UV source are triggered simultaneously, but the image capture device is configured with a delay, which ensures that capture begins as soon as the UV lamp pulse has ended. This excludes any fluorescence produced during excitation so that only short-lived phosphorescence is captured. The process is repeated so that multiple lamp pulses occur and multiple phosphorescence captures are taken between the pulses. In this way, multiple excitations of the sample occur and multiple phosphorescence measurements can be taken within a short time frame. These multiple measurements can then be combined to produce a composite image which is suitable for analysis by an operator.

Figure 2:
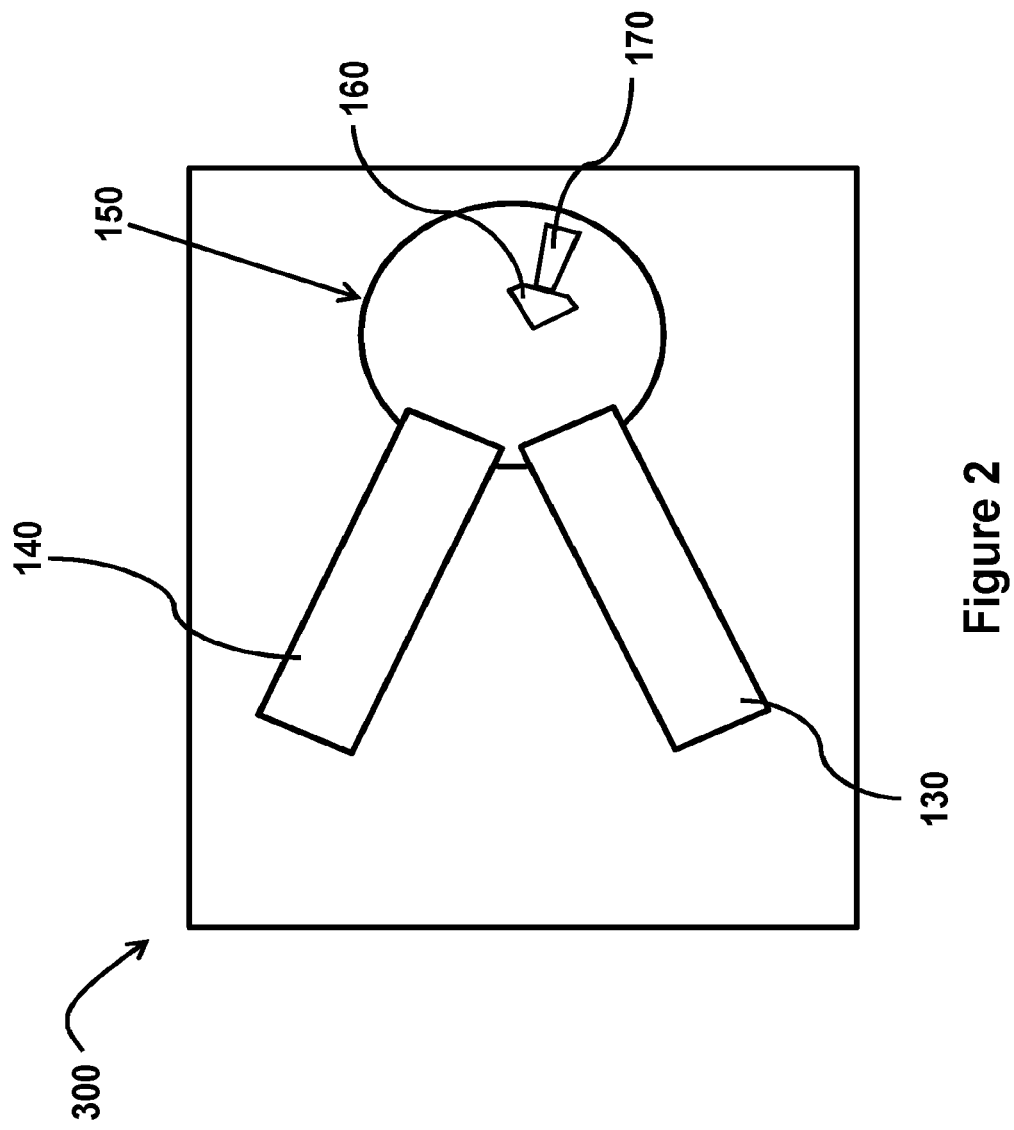
FIG. 2 is a schematic representation of an apparatus for measuring fluorescence and/or short-lived phosphorescence.

FIG. 2 is a schematic representation of an apparatus 300 for measuring luminescence properties of a diamond 160 so as to provide an indicator as to whether a diamond is natural and/or the type of the diamond. The apparatus 300 comprises a source of electromagnetic radiation 130 at wavelengths of substantially 225 nanometers (nm) or less, a light detection device 140 for capturing any visible light emitted by the diamond 160 and a control system (not shown) to synchronise the operation of the source 130 and light detection device 140. The control system configures the source 130 to repeatedly irradiate the diamond 160 with multiple excitation pulses of electromagnetic radiation, and the light detection device 140 to capture any visible light emitted to produce image data during time windows, each having a predetermined time relationship relative to an excitation pulse, each time window being closed before the start of the next excitation pulse, so as to obtain luminescence data. A processor (not shown) may be configured to combine the luminescence data from the multiple associated with all of the pulses.

The diamond sample 160 to be tested is held on a sample holder 170 within a chamber 150. The surface of the sample 160 is irradiated by the electromagnetic source (lamp) 130. The source 130 and the light detection device 140 are configured by the control system to repeatedly irradiate the diamond 160 and capture any visible light emitted in multiple exposure windows to produce multiple captures.

In one suitable arrangement the electromagnetic source (lamp) and light detection device (camera) are triggered simultaneously by a standard transistor to transistor logic (TTL) signal. The signal is variable up to the maximum frame rate of the camera and depending upon the timescales for measurement that are required. The synchronised, simultaneous triggering of the lamp and camera is automatic and independent of operator control, due to the very short timescales involved.

In this example, a TTL signal is sent from a pulse generator (not shown here). The maximum repetition rate is governed by the maximum pulse frequency of the lamp, or the maximum frame rate of the camera, whichever is the lower.

Both camera and lamp trigger on the leading edge of the pulse. Ideally, and ignoring any delay in the lines, the triggering would be exactly simultaneous, but typically the camera has an offset value which is quoted by the manufacturer. The exposure time is limited by frequency of the pulse generator, i.e. 10 Hz gives a time window of 100 milliseconds minus the effective delay.

The ultraviolet source 130 used in this example is a microsecond xenon spark lamp, such as a Perkin Elmer FX-1165, filtered to provide above diamond band-gap excitation at wavelengths of less than 225 nm. The lamp pulse rate can be configured by an operator via the control system. For the purposes of this example a suitable pulse length for the excitation is 80 µs.

The camera 140 in this example makes use of a complementary metal oxide semiconductor (CMOS) sensor, such as the Sony IMX174 which can be configured by the control system with a delay, such that the camera captures visible light during a time window which opens after the associated excitation pulse has ended. Thus, any fluorescence emitted by the diamond sample 160 is filtered out. Such fluorescence would potentially mask any short-lived phosphorescence. The length of the delay in recording (i.e. the time window start time relative to the excitation pulse start) can be set by an operator, as can the length of recording (i.e. length of time window) and the number and/or frequency of excitation pulses, using the control system. One or more of these parameters may be operator controllable via the control system.

For the camera 140 in this example, the offset described above is 26 µs. Adding in an additional delay of 54 µs, gives an effective delay of 80 µs which is sufficient to ensure each lamp pulse has ended before capture of phosphorescence begins. This filters out any fluorescence which could mask short-lived phosphorescence. It will be appreciated that it may be beneficial to allow for a short delay of a few microseconds between the end of the excitation pulse and the start of the time/exposure window.

It will be appreciated that although the camera 140 and UV source (lamp) 130 are synchronised, or triggered simultaneously, the camera 140 does not begin to record until the delay time has expired i.e. until the lamp pulse has ended. Synchronising the UV source 130 and camera 140 in this way allows the measurement of short-lived phosphorescence which typically occurs for less than 80 milliseconds after excitation from the pulse has ended. Due to the very short timescales involved, a camera which was not triggered until after the pulse had ended would typically be unable to capture this rapid phosphorescence.

The number of recordings or captures can be varied by an operator. The luminescence data from the multiple phosphorescence captures is combined by a processor to create an image of the diamond, suitable for visual analysis i.e. a visible spectrum colour image of any phosphorescence produced. This may be carried out by software hosted on a PC (not shown here). Alternatively, apparatus for combining these captures may be integral to an apparatus 300 such as that shown in FIG. 2. Alternatively or additionally, an image analyser may be included for analysing the combined luminescence data.

Typically, image data from around forty captures, stored as jpeg images, may be averaged in order to produce a composite image of any short-lived phosphorescence produced by the sample 160. Combining multiple images also reduces signal to noise ratio and improves image quality.

Certain diamond samples may require greater or fewer captures to be combined in order to produce an image suitable for analysis.

The composite colour image is then presented for analysis by an operator or user. In this example, the image is presented via a PC screen (not shown here), but the apparatus 300 shown in FIG. 2 may be adapted to include an image display device, such as a screen or monitor, suitable for viewing and analysing the composite image. The operator would typically have received training or have access to information to assist in this analysis.

As discussed above, it is possible to distinguish between natural and synthetic diamond through measurement of short-lived, weak phosphorescence. Typically, such phosphorescence exhibits a broad emission with a peak at 450 nm and a decay time of less than 80 ms. Where analysis of an image of the diamond, produced by the apparatus above, confirms the presence of blue phosphorescence in a time window starting at or after the end of the excitation pulse (around 80 μs) and finishing at around 80 ms excitation pulse, this is an indicator that the diamond sample being tested is a natural Type IIa or weak Type Ia diamond.

Alternatively or additionally, where analysis of an image of the diamond confirms the presence of turquoise phosphorescence in a time window of between around 80 ms and 500 ms after an excitation pulse, this is an indicator that the diamond sample being tested is a weak Type IIb diamond. The longer-lived (slow) turquoise phosphorescence in this case is due to boron impurities. Typically, such phosphorescence exhibits a broad emission with a peak at 480 nm.

Where analysis of an image of the diamond confirms the presence of green phosphorescence in a time window of between around 80 ms and 500 ms after an associated excitation pulse, this is an indicator that the diamond sample should be referred for further testing. Such slow green phosphorescence typically exhibits a structured emission with a peak at 530 nm to 550 nm.

If long integration times and excessively high detector gains do not produce a meaningful spectrum, the stone should be referred for further tests. In other words, where analysis of an image of the diamond, as produced by the above apparatus, confirms negligible luminescence in a time window configured to begin after the excitation pulse has ended, this is an indicator that the diamond should be referred for further testing.

The composite image produced by the method and apparatus 300 in the example described above typically comprises an actual colour image of visible phosphorescence, rather than illustrating spectra or decay times, and is therefore suitable for qualitative analysis. It will be appreciated that, rather than (or as well as) producing composite images, the instrument may be configured to perform spectral analysis of the light emitted by the stone. A spectrum may be obtained for each time window discussed above, and averaged over many pulses. The spectroscopic features described above can be identified by a user or automatically by the processing unit. If automatic identification is provided, the instrument can provide an automatic indication to a user as to whether the diamond is likely to be natural or whether it should be referred for further testing.

Figure 3:
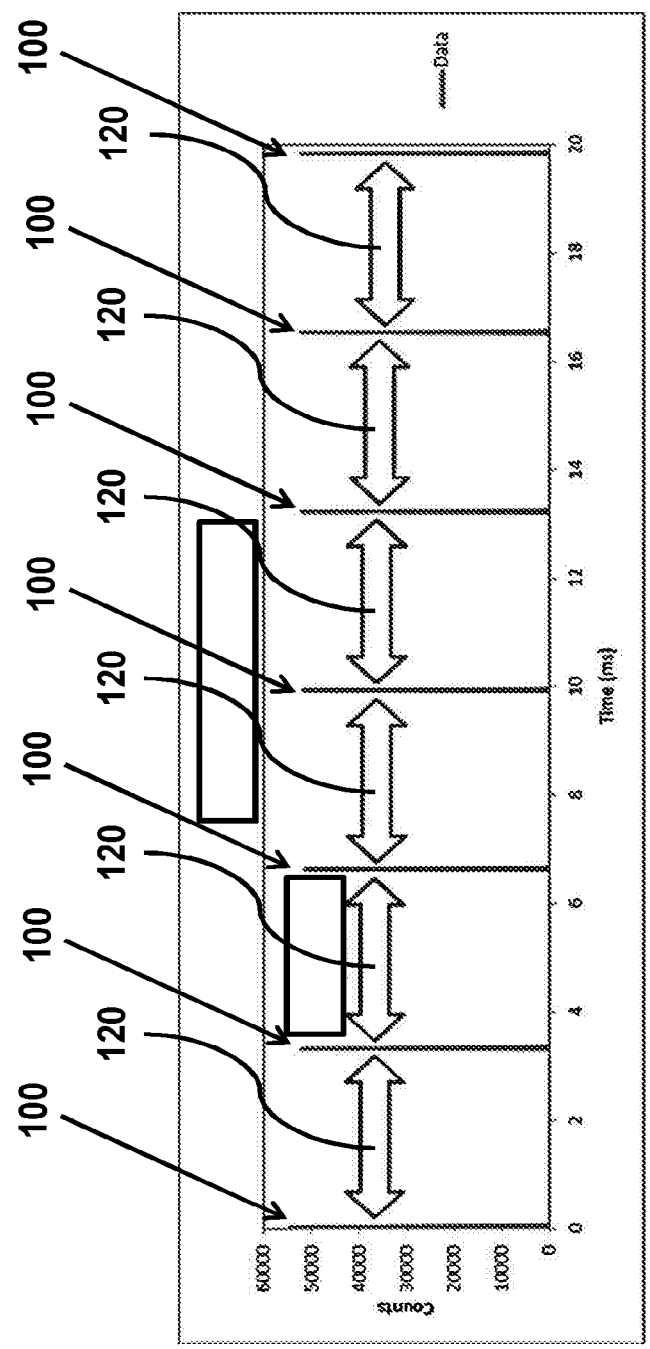
FIG. 3 is a graphical representation of a method of measuring short-lived phosphorescence.

FIG. 3 is a graphical representation of a method of providing an indicator for a diamond as to whether it is natural and/or what type it is by testing for the presence or absence of one or more specific markers in the luminescence properties of the diamond. These markers are characterised by luminescence decay time and luminescence wavelength.

The method comprises irradiating the diamond with multiple excitation pulses of electromagnetic radiation 100; and during and/or following each excitation pulse 100, detecting light emitted by the diamond in at least one time window 120 having a predetermined time relationship relative to that excitation pulse 100, each time window 120 being closed before the start of the next excitation pulse 100, so as to obtain luminescence data. Each time window 120 is chosen to include luminescence having a decay time characteristic of one or more of the above-mentioned markers. The luminescence data is analysed in order to establish the presence or absence of the one or more markers. The method further comprises combining the luminescence data associated with all of the pulses 100.

In this illustrated example, the method further comprises synchronising light detector with a source of ultraviolet excitation pulses 100, and capturing light in the visible spectrum emitted by the diamond to produce luminescence data for each pulse 100; and combining the luminescence data obtained in a specific time window associated with each excitation pulse to create an image of any luminescence emitted by the diamond in that time window. This image is suitable for visual analysis, and includes a colour image of the diamond.

In the example of FIG. 3, each time window 120 is opened after the associated excitation pulse 100 has ended, so that the luminescence data comprises phosphorescence data. Multiple phosphorescence captures are taken in time windows 120 between multiple UV source pulses 100, over a millisecond time frame. These multiple captures are combined to build up an image of any luminescence produced by the sample as a result of UV excitation. Suitable pulse lengths for the excitation include pulse lengths in the range 50 μs to 150 μs.

In this example, the irradiation of the diamond 100 and the light capture are triggered substantially simultaneously, as described above.

Figure 4:
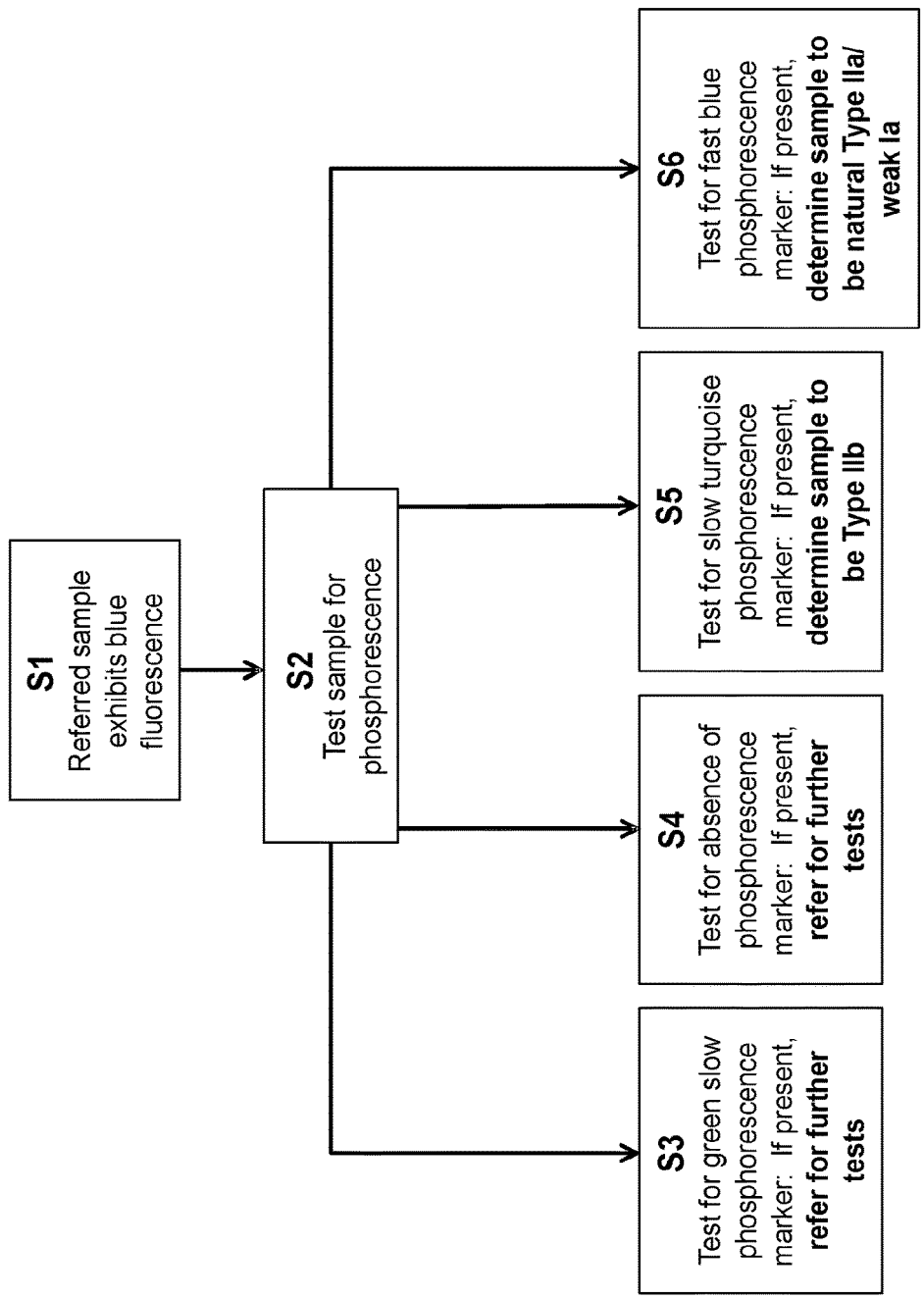
FIG. 4 is a flow diagram of a method of determining whether a diamond is natural.

FIG. 4 is a flow diagram illustrating a method of determining whether a diamond is natural, by testing for the presence or absence of one or more specific markers in the phosphorescence properties of the diamond. Normally, diamond tested by this method would have been referred for further testing by a screening method such as UV/Visible absorption. The following numbering corresponds to the numbering of FIG. 4.

S1. Sample exhibits blue fluorescence: a diamond sample which exhibits blue fluorescence under conventional testing is selected for further testing.

S2. Test sample for phosphorescence: the sample is irradiated with multiple excitation pulses from an electromagnetic source, as described with reference to FIG. 3 above. Multiple measurements or captures are taken of any luminescence produced, in time windows which open after each associated excitation pulse has ended. The time window is selected in order to test for one or more specific markers, as described above. Luminescence data comprising phosphorescence data from these multiple captures is combined to produce a composite image, suitable for analysis by an operator.

S3. Test sample for green slow phosphorescence marker: test for green phosphorescence in a time window between around 80 ms and around 500 ms after the start of the associated excitation pulse. Where analysis of the composite image shows that green phosphorescence in this time window is present, this is an indicator that the sample should be referred for further testing (not described here). Typically, this slow green phosphorescence exhibits structured emission with a peak at around between 530 nm to 550 nm.

S4. Test sample for negligible or absence marker: where analysis of the composite image shows that the sample exhibits no, or negligible, phosphorescence, this is an indicator that the sample should be referred for further testing.

S5. Test sample for slow turquoise phosphorescence marker: test for turquoise phosphorescence in a time window between around 80 ms and around 500 ms after the start of the associated excitation pulse. Where analysis of the composite image shows that the sample exhibits slow turquoise phosphorescence, the sample is determined to be natural diamond, usually a natural special case weak Type IIb diamond, and no further testing is required. Typically, this slow turquoise phosphorescence exhibits a broad emission with a peak at around 480 nm.

S6. Test sample for fast blue phosphorescence marker: test for blue phosphorescence in a time window between around 80 µs and around 80 ms after the start of the associated excitation pulse. Where analysis of the composite image shows that the sample exhibits fast blue phosphorescence, the sample is determined to be natural diamond, usually a natural Type IIa or weak Ia diamond, and no further testing is required. Typically, this fast blue phosphorescence exhibits a broad emission with a peak at around 450 nm.

Additionally or alternatively to the markers described with reference to FIG. 4 above, the presence or absence of further markers may be determined using the method disclosed herein.

For example, the sample may be tested for an orange long lived fluorescence marker, comprising luminescence having a wavelength between about 535 nm and about 600 nm and a decay time of less than 1 millisecond. The presence of the orange long lived fluorescence marker is an indicator that the sample should be referred for further testing.

The sample may additionally or alternatively be tested for a red phosphorescence marker, comprising luminescence having a wavelength between about 575 nm and about 690 nm and a decay time of greater than 1 millisecond. The presence of the red phosphorescence marker is an indicator that the sample should be referred for further testing.

The sample may additionally or alternatively be tested for a weak green fluorescence marker having a wavelength of about 510 nm. Testing for the weak green fluorescence marker comprises testing in a time window which is synchronised with the excitation pulse, and the presence of the weak green fluorescence marker is an indicator that the sample should be referred for further testing.

Figure 5:
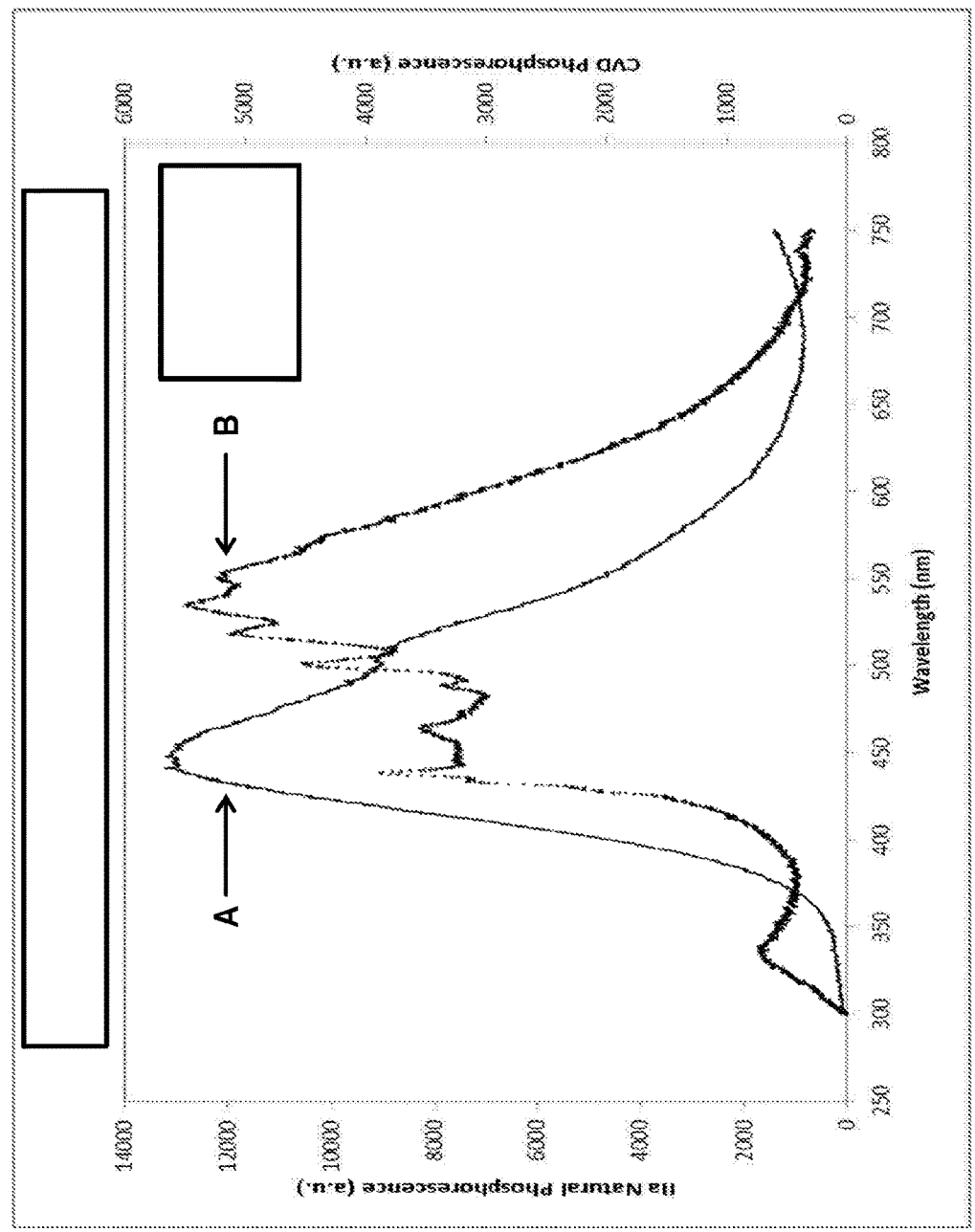
FIG. 5 is a graphical representation of short-lived phosphorescence spectra of a Type IIa natural diamond sample and a CVD synthetic diamond sample.

FIG. 5 is a graphical representation of the short-lived phosphorescence spectra of a Type IIa natural diamond sample A and a CVD synthetic diamond sample B. Both samples are round brilliant cut and less than 1 carat. The CVD synthetic sample exhibits mainly blue fluorescence (not shown here) with a colour and spatial distribution similar to that seen in natural diamonds.

Spectrum A is the short-lived phosphorescence spectrum of the Type IIa natural diamond sample. Spectrum B is the short-lived phosphorescence spectrum of the synthetic CVD diamond sample. Both exhibit short-lived phosphorescence which occurs for less than 100 milliseconds after removal of the source of electromagnetic radiation.

This spectral analysis demonstrates that the short-lived or fast phosphorescence produced by a natural, untreated Type IIa diamond is blue, broad and peaks at around 450 nm. This type of short-lived phosphorescence is not seen in samples of synthetic diamond, which either show negligible or weak green short-lived phosphorescence. Spectrum B as shown in FIG. 5 demonstrates that the synthetic CVD diamond sample in this example exhibits weaker, short-lived or fast green phosphorescence, which peaks at around 530 nm to around 550 nm.

Figure 6:
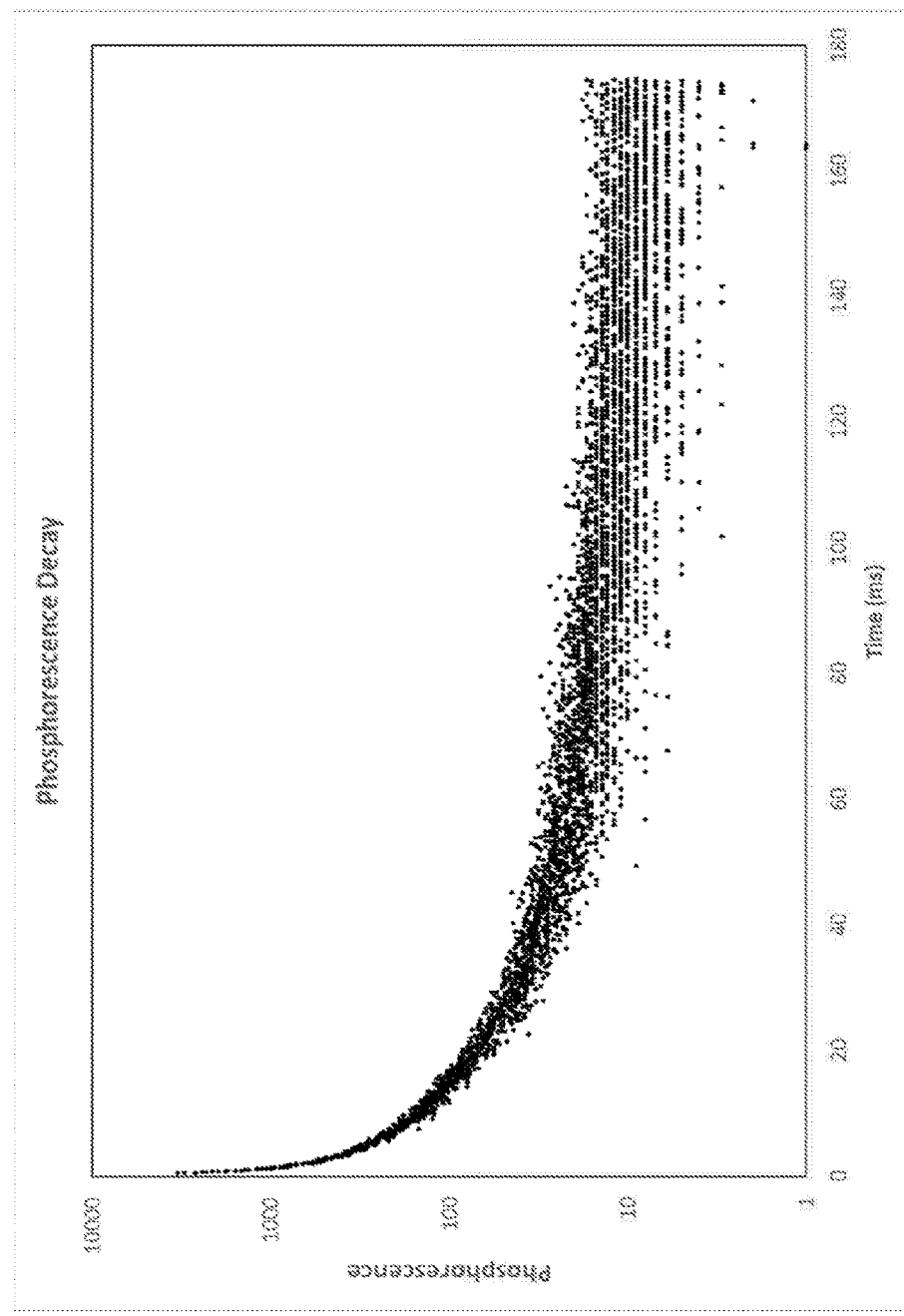
FIG. 6 is a graphical representation of phosphorescence over time in a sample of natural diamond.

FIG. 6 is a graphical representation of phosphorescence decay in a sample of natural, untreated Type IIa diamond. Such diamonds form around 1-2% of all natural diamonds, and are almost completely free of impurities. It can be seen from the graph that the phosphorescence recorded from this UV-excited sample is relatively short-lived, decaying at less than 80 milliseconds after initial excitation (at time zero). Short-lived phosphorescence of this type would not be detected using conventional diamond identification techniques, since it decays before conventional phosphorescence capture begins. It can, however, be imaged using the method and apparatus described above.

Figure 7:
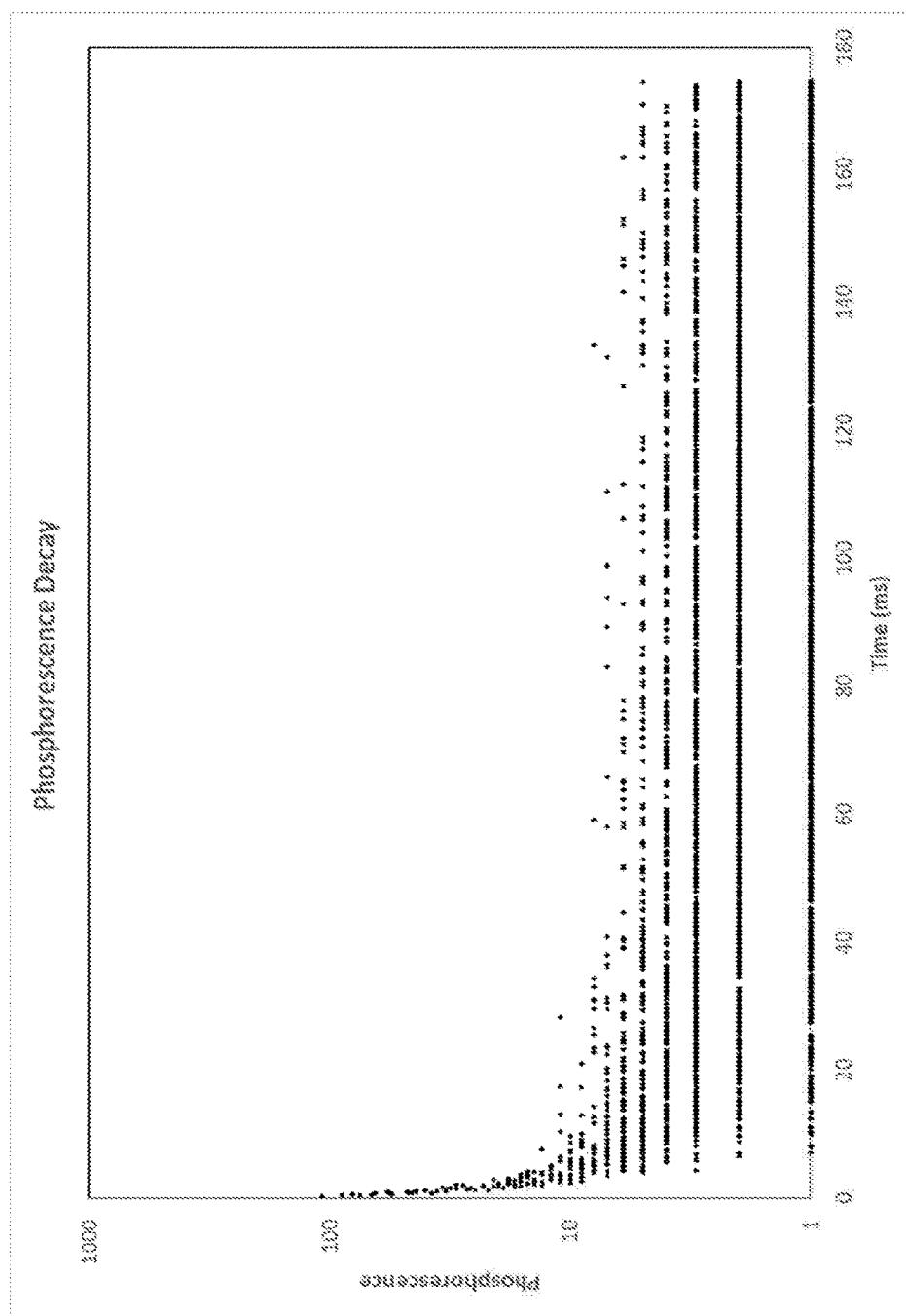
FIG. 7 is a graphical representation of phosphorescence over time in a sample of synthetic diamond.

FIG. 7 shows phosphorescence decay in a sample of high purity synthetic CVD diamond. It can be seen that the short-lived or fast phosphorescence produced from this synthetic sample under the same conditions is negligible in comparison with the sample of natural diamond shown in FIG. 6 above.

Analysis of a composite image of short-lived phosphorescence in a diamond, produced by the method and apparatus described herein, therefore enables a trained operator to distinguish between a natural and a synthetic diamond sample. This is the case even where the two samples would produce similar results using conventional imaging techniques.

The methods and apparatus described above improve the ability to distinguish between natural and synthetic through the measurement of short-lived phosphorescence. However, the imaging of prompt fluorescence can also provide valuable information regarding the presence of other luminescent centres or an indication of the arrangement of lattice dislocations. This information can assist in determining whether a diamond is natural or synthetic, as previously discussed.

Figure 8B:
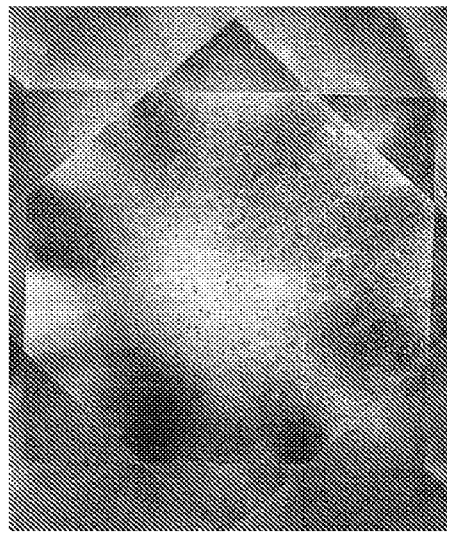
FIG. 8b is a synchronised image of UVC excited luminescence in a natural diamond sample.
Figure 8A:
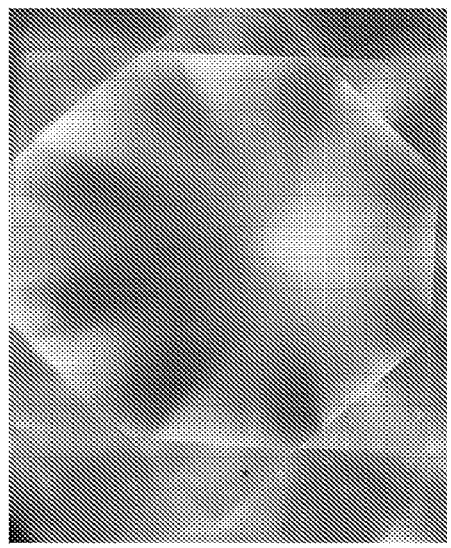
FIG. 8a is an unsynchronised image of UVC excited luminescence in a natural diamond sample.

FIGS. 8a and 8b are images of UVC excited luminescence produced by the same 1.53 carat round brilliant type IIb natural diamond. Such diamonds often contain trace elements of boron, in common with some HPHT and CVD synthetic diamonds.

FIG. 8a shows an image of relatively long-lived or slow phosphorescence produced by the above type IIb natural diamond under UVC excitation. The image was obtained using conventional methods of diamond identification, in which the UV source and camera are unsynchronised, and a single long capture of all types of luminescence (fluorescence, short-lived phosphorescence, long-lived phosphorescence) is taken. The green, long-lived (or slow) phosphorescence produced by the diamond in this example is strong. Since the camera is recording total luminescence and the duty cycle of the excitation is low, the strong phosphorescence swamps any fluorescence which may be produced during the excitation pulse.

FIG. 8b shows the sample of FIG. 8a, but in this example the UV source and camera are synchronised to the same pulse length so that image capture takes place only when the diamond is illuminated by UVC light. In this image, which is produced by averaging around 50 captures, prompt blue fluorescence is visible. This fluorescence, which was masked in the image of FIG. 8a, is produced by the arrangement of the diamond lattice dislocations.

As an alternative (or in addition) to producing a composite image by averaging images associated with many excitation pulses, it will be appreciated that images obtained from individual pulses can be displayed to a user in sequence. This may be at the pulse rate, or it may be that the images from several pulses can be captured and then displayed to the user as a video at a higher frame rate. It is also possible for the system to be set up for a user to trigger one or a series of pulses manually so as to obtain an image or composite image, and then to trigger further pulses or series of pulses to obtain a further image or composite image. Each image or composite image would be obtained in the same time window relative to its associated excitation pulse, so would be of luminescence having a particular decay characteristic, chosen to represent one of the markers discussed above. A skilled user can thus study an image or composite image and choose to obtain further images to identify if a colour or feature under consideration is real or is an artefact of the image currently under consideration.

Prompt fluorescence may be captured using the same apparatus as described in FIG. 2 above, but modifying the delay applied to the light detection device. The apparatus comprises a source of electromagnetic radiation at wavelengths of substantially 225 nanometers or less, a light detection device for capturing any visible light emitted by the diamond and a control system. The source and the light detection device are synchronised by the control system and configured to repeatedly irradiate the diamond with excitation pulses of electromagnetic radiation and to capture any visible light emitted by the diamond during time windows each having a predetermined time relationship relative to an excitation pulse, each time window being closed before the start of the next excitation pulse, so as to obtain luminescence data. A processor is configured to combine the luminescence data associated with all of the pulses. In the example of FIG. 8b, the control system configures the light detection device to capture visible light during a time window which opens at the same time as the associated excitation pulse begins and which closes before or at the same time as the associated pulse ends. Suitable excitation pulse lengths are again in the range 50 μs to 150 μs. An image analyser is used to analyse the combined luminescence data.

Figure 9:
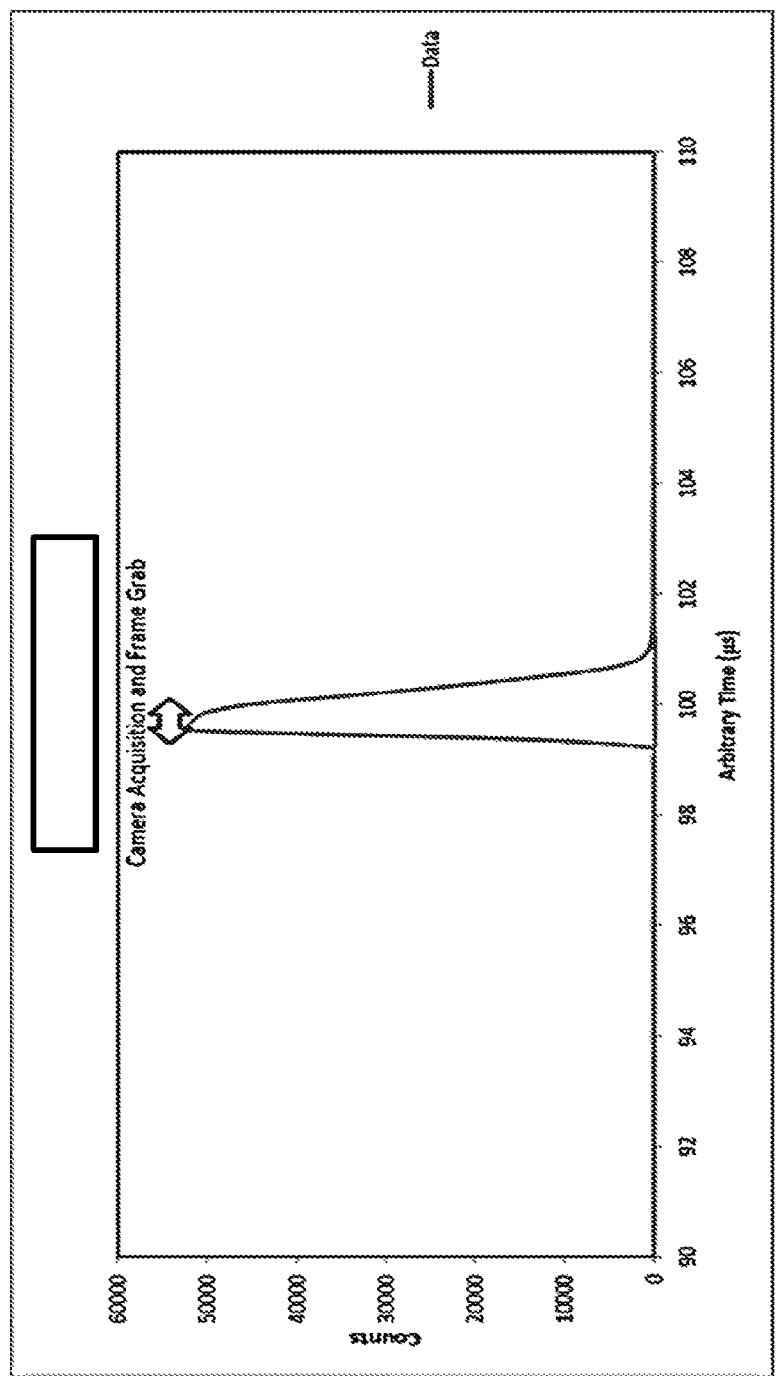
FIG. 9 is a graphical representation of a method of measuring prompt fluorescence in a diamond.

FIG. 9 is a graphical representation of a method of measuring prompt fluorescence, comprising opening a time window at the same time or very shortly after the start of the associated excitation pulse and closing this time window before or at the same time as the associated pulse ends, so that the luminescence data obtained comprises fluorescence data. In this example, the UV source or lamp/strobe pulse is synchronised with the light detection device (camera/photodetector). Measurements are taken over microsecond time scales.

The method of measuring prompt fluorescence differs from that of measuring short-lived phosphorescence, as described in FIGS. 2 to 8 above. In the example of FIG. 9, the lamp pulse and camera are substantially synchronised, however, the camera is not configured with a delay (other than the manufacturer's offset). The camera exposure time is set to exactly coincide with the lamp pulse width. Capture of prompt fluorescence therefore occurs only during the microsecond lamp pulse i.e. only during excitation of the sample. Since short-lived phosphorescence occurs for around 100 milliseconds after the UV source has been removed i.e. after the lamp pulse, this phosphorescence is filtered out of the prompt fluorescence measurement.

Therefore fluorescence is only measured during the excitation pulse, while short-lived phosphorescence is only measured between excitation pulses. In both cases, the lamp and the light detection device are synchronised. In order to measure short-lived phosphorescence, however, a delay is applied to the light detection device to allow the excitation pulse to end before detection begins.

Figure 10:
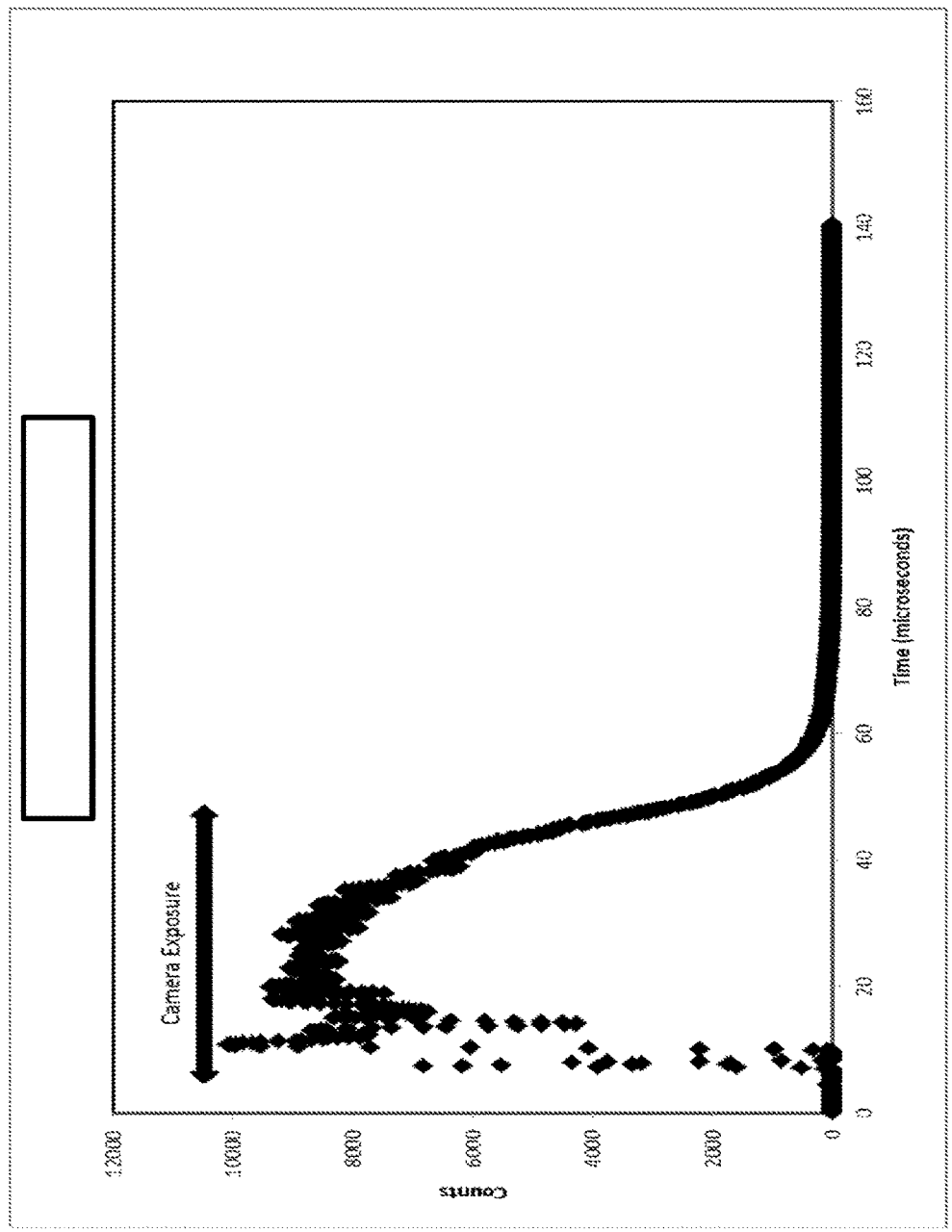
FIG. 10 is a graphical representation of a typical lamp pulse width and corresponding fluorescence measurement.

FIG. 10 illustrates a typical xenon flash lamp pulse width, used to provide UVC excitation of a diamond sample. The usable pulse width is approximately 50 microseconds, therefore this is the maximum length of the exposure window used to capture fluorescence only, as shown. Since the camera is configured to record only during the lamp pulse, any phosphorescence which might otherwise obscure the fluorescence emitted by the diamond is gated out. The gap between the pulses in fluorescence mode is determined by the maximum frame rate of the camera. For example, a Sony IMX174 CMOS sensor may be used, which at full resolution can deliver a maximum frame rate of over 40 Hz.

The same apparatus may be used for the measurement of short-lived phosphorescence and prompt fluorescence. The operator can control the delay in capture i.e. the time window start time relative to the excitation pulse start, therefore the camera can be configured without a delay in order that the capture occurs during the excitation pulse. The lamp and camera are substantially synchronised by a TTL signal, as described above.

Figure 11A:
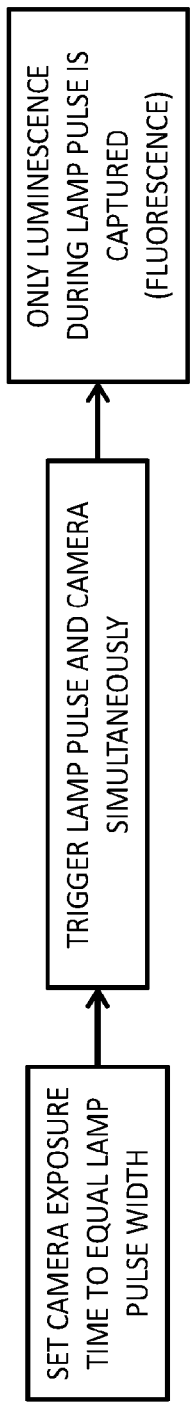
FIG. 11a is a flow diagram illustrating a first configuration for operation of the apparatus of FIG. 2.
Figure 11B:
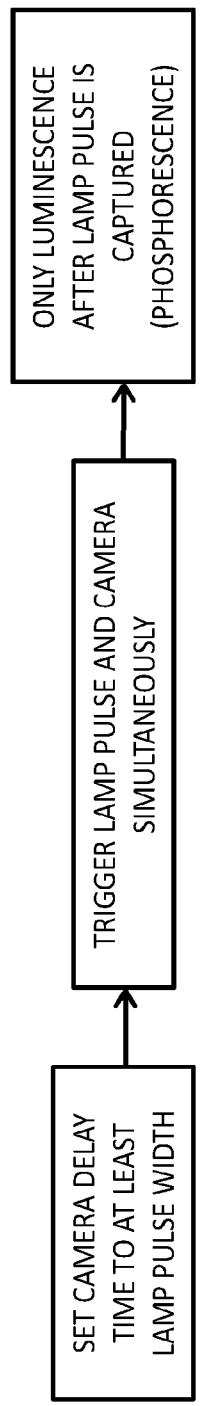
FIG. 11b is a flow diagram illustrating an alternative configuration for operation of the apparatus of FIG. 2.

FIGS. 11a and 11b are flow diagrams illustrating two different configurations of the apparatus described in FIG. 2 above. FIG. 11a illustrates measurement of prompt fluorescence, in which the exposure window for luminescence capture begins at the same time as the lamp pulse, and ends before or at the same time as the pulse. Any phosphorescence produced after excitation is therefore filtered out. Conversely, FIG. 11b illustrates measurement of phosphorescence, in which the exposure window for luminescence capture is delayed until after the lamp pulse has ended, and fluorescence is filtered out. It will be appreciated that in both cases, the lamp pulse and capture may be repeated, as required, and a composite image produced from luminescence data produced from the multiple pulses. The composite image may be generated simply by averaging RGB (or HLS values) for each pixel in the individual captures or may be more sophisticated than that.

Multiple captures of prompt fluorescence may be carried out, which can then be combined to produce a colour, visible spectrum image of prompt fluorescence, suitable for analysis by an operator. This may be done in the same way as described above i.e. by averaging typically around forty captures. The image may be analysed in order to determine whether a diamond sample is natural or synthetic based upon analysis of the presence or absence of luminescence centres and/or the arrangement of lattice dislocations.

The methods and apparatus described above provide an operator with the facility to alter various aspects of the measurement process. For example, the delay in capture following the UV pulse (the time window start time relative to the excitation pulse start), the exposure time window (length of time window), and the excitation pulse repetition rate (number and frequency of pulses) are all controllable by the operator. This allows the measurement of rapid phosphorescence at various intensities and decay times, depending upon the sample which is undergoing evaluation.

Figure 12:
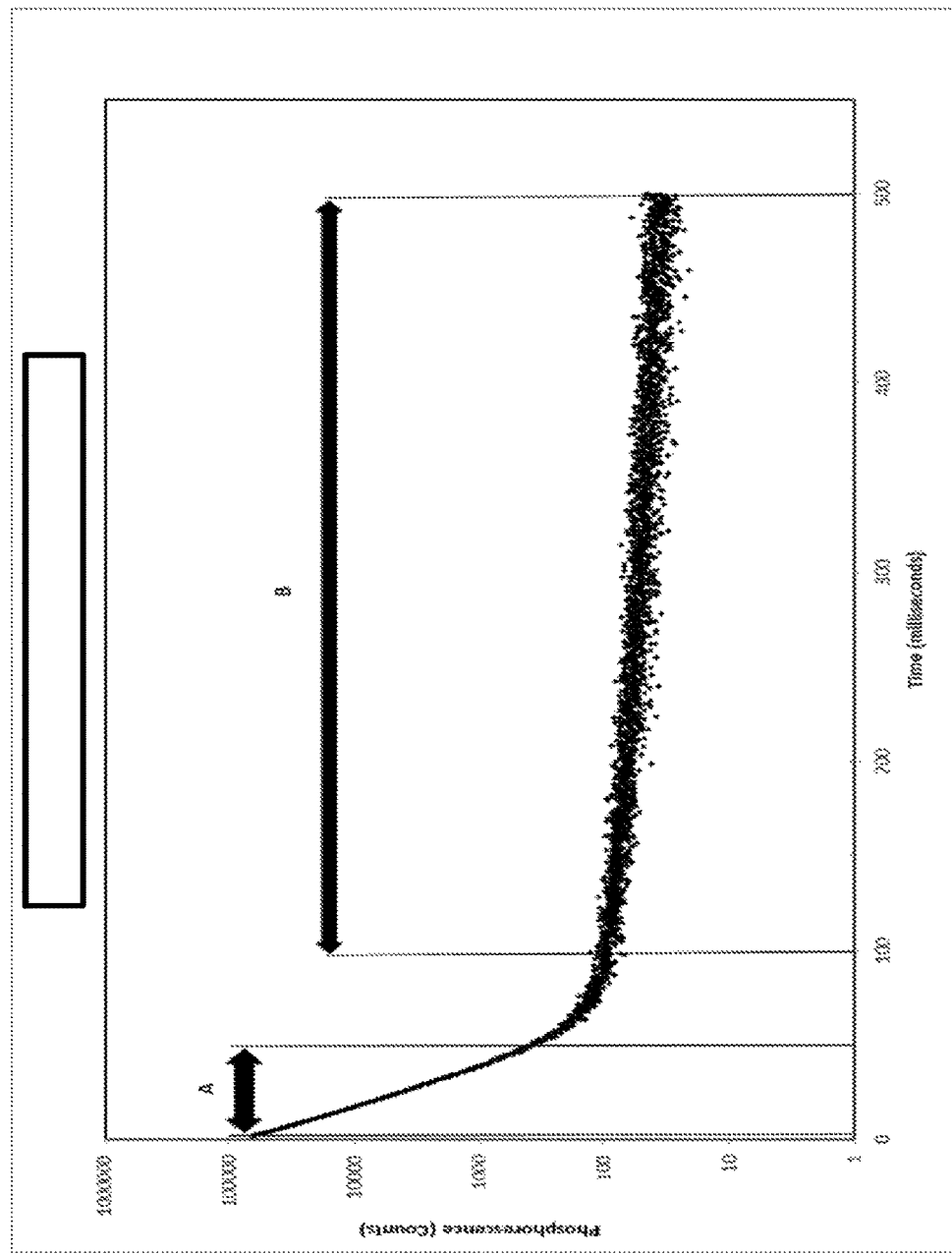
FIG. 12 is a graphical illustration of a method of isolating phosphorescence components.

FIG. 12 illustrates phosphorescence decay over time of a natural diamond, following UVC excitation at room temperature, demonstrating two clear phosphorescence components, indicated by regions of interest A and B. Region A represents short-lived, fast phosphorescence which decays at 80 milliseconds or less, while region B represents slow phosphorescence at decay times of greater than 100 milliseconds. Varying acquisition parameters as described above allows the two components to be isolated.

Where an operator wishes to establish the presence or absence of short-lived phosphorescence, a short capture delay and short exposure window may be used. In the example of FIG. 12 (region A), a capture delay of 80 microseconds is applied, with a camera exposure time of 50 milliseconds. The UV strobe frequency and camera frame rate are set to 20 Hz maximum. The delay of 80 microseconds ensures that the lamp pulse, typically 50 microseconds long, has ended before capture begins, filtering out any fluorescence.

Alternatively, if an operator wishes to investigate whether phosphorescence at decay times of greater than 100 milliseconds is present, a longer capture delay is used. In the example of FIG. 12 (region B), a capture delay of 100 milliseconds is used, with a camera exposure time of 400 milliseconds. The strobe frequency and camera frame rate are set to 2 Hz maximum. The delay of 100 milliseconds ensures that any short-lived phosphorescence has dissipated so that only longer-lived or slow phosphorescence is captured.

Thus, the time window may be set in order to test for one or more specific markers in the luminescence properties of the diamond, characterised by decay time and wavelength.

It will be appreciated that the lamp pulse and phosphorescence capture shown in FIG. 12 may be repeated multiple times in order to acquire multiple sets of luminescence data which can be combined to produce an image suitable for analysis.

It is envisaged that the method and apparatus described herein may be used in conjunction with conventional identification methods and integrated with conventional identification apparatus. It may therefore be employed as an additional test or tests in an existing identification process. It is intended that both mounted and loose stones may be investigated by the above method and apparatus. This may be primarily for gemstone identification or valuation, or for industrial or scientific research purposes.

It will be appreciated by the person skilled in the art that various modifications may be made to the above described embodiment, without departing from the scope of the present invention.

For example, the multiple phosphorescence/fluorescence measurements produced by the above method and apparatus may be combined and/or enhanced by any suitable means in order to create an image of any visible short-lived phosphorescence or prompt fluorescence emitted, which can then be analysed to determine the nature of the diamond sample. The multiple captures may be combined after all measurements are complete, or they may be combined as the measurements are being taken. The image or images so produced may be analysed by an operator via a screen or display of any suitable type.

Alternatively, the apparatus may be configured to display or otherwise convey a determination as to the type of diamond under analysis, for example, by indicating visually or audibly that the sample has passed or failed the identification process, or that further analysis is required. The combined images or video may be presented to the operator in colour or in black and white.

Alternative sources of electromagnetic radiation (lamps, strobes) such as a Perkin Elmer FX-1165 flashtube, may be used. Any suitable method of synchronising the source and light detection device may be used.

The capture delay configured by the operator may be varied as required depending upon the offset value for different types of camera, photodetector or image capture device. The effective delay may typically be between 40 and 100 microseconds, optionally 80 microseconds, but this may be reduced or increased as needed. This effective delay may include or exclude the built-in camera offset value.

Measurement of fluorescence and/or short-lived phosphorescence using the methods and apparatus described herein may be carried out separately or may be combined.

As used herein, natural is defined as a stone from nature consisting exclusively of diamond produced by geological processes. The term natural, as defined herein, indicates that the stone is not synthetic, but does not exclude the possibility that the stone could have been treated, for example by pressure or heat treatment, unless specifically stated.

As used herein, synthetic is defined as a man-made stone consisting exclusively of diamond produced by artificial or industrial processes, such as chemical vapour deposition or high pressure high temperature processes.

As used herein, treated is defined as a natural stone (as defined above) which has been modified in order to improve its colour or clarity, for example by chemical or mechanical means, by irradiation or by pressure or heat treatments.

As used herein, type is defined using the standard diamond classification system which separates stones based on their physical and chemical properties, e.g. Type Ia, Type IIb etc.

The measurement of fluorescence and of rapid, short-lived phosphorescence on millisecond timescales, using the methods and apparatus described above, reduces the potential for synthetic diamonds to be incorrectly identified as natural. Additionally, the number of diamond samples requiring further investigation or analysis by other methods is reduced.

The invention claimed is:

1. A method of providing an indicator for a diamond as to whether it is natural by testing for the presence or absence of one or more specific markers in the luminescence properties of the diamond, said markers characterized by luminescence decay time and luminescence wavelength, the method comprising:
   irradiating the diamond with at least one excitation pulse of electromagnetic radiation;
   during and/or following the excitation pulse, detecting light emitted by the diamond in at least one time window having a predetermined time relationship relative to the excitation pulse so as to obtain the luminescence data, the or each time window being chosen to include luminescence having a decay time characteristic of one or more of the specific markers; and
   obtaining an image from luminescence data associated with the one or more specific markers for each time window associated with the excitation pulse.

2. The method of claim 1, further comprising displaying the image to a user.

3. The method of claim 1, comprising testing for the presence or absence of more than one specific marker.

4. The method of claim 1, further comprising analyzing the luminescence data in order to establish the presence or absence of one or more of the specific markers.

5. The method of claim 1, comprising displaying to a user the image from a specific time window.

6. The method of claim 5, wherein images from each time window are displayed to the user in the form of a video.

7. The method of claim 1, further comprising synchronizing a source of the excitation pulses with a light detector.

8. The method of claim 1, further comprising opening a time window after the associated excitation pulse has ended, so that the luminescence data comprises phosphorescence data.

9. The method of claim 1, further comprising opening a time window at the same time or very shortly after the start of the associated excitation pulse and closing said time window before or at the same time as the associated pulse ends, so that the luminescence data comprises fluorescence data.

10. The method of claim 1, wherein one of the one or more markers is a blue fast phosphorescence marker comprising luminescence in a wavelength band peaking at about 450 nm and a decay time of less than about 80 ms.

11. The method of claim 10, wherein testing for the blue fast phosphorescence marker comprises testing, in a time window opening at or after the end of the excitation pulse and ending about 80 milliseconds after the end of the associated excitation pulse, for a luminescence band peaking at about 450 nm.

12. An apparatus for providing a visual indicator as to whether a diamond is natural by measuring luminescence properties of the diamond, the apparatus comprising:
- a source of electromagnetic radiation;
- a light detection device for capturing visible light emitted by the diamond;
- a control system configured:
  - to synchronize the source and light detection device;
  - to cause the source to irradiate the diamond with at least one excitation pulse of electromagnetic radiation; and
  - to cause the light detection device to capture visible light emitted by the diamond during at least one time window having a predetermined time relationship relative to the excitation pulse so as to obtain luminescence data; and
- a processor configured to process the captured visible light to obtain an image of the luminescence data for each time window associated with the excitation pulse;
- wherein the or each time window is chosen to encompass one or more specific markers in the luminescence properties of the diamond, said markers characterized by luminescence decay time and luminescence wavelength and providing an indicator of whether the diamond is natural.

13. The apparatus of claim 12, further comprising a display device for displaying the image to a user.

14. The apparatus of claim 12, wherein the at least one time window includes one or more time windows chosen to encompass a plurality of specific markers.

15. The apparatus of claim 12, wherein the control system is configured to cause the source to irradiate the diamond repeatedly with a series of excitation pulses, and wherein the at least one time window is associated with each excitation pulse and is configured to close before the start of a subsequent excitation pulse.

16. The apparatus of claim 12 and configured to measure phosphorescence in a diamond, wherein the control system configures the light detection device to capture visible light during a time window which opens after the associated excitation pulse has ended.

17. The apparatus of claim 12 and configured to measure fluorescence in a diamond, wherein the control system configures the light detection device to capture visible light during a time window which opens at the same time as the associated excitation pulse begins and which closes before or at the same time as the associated pulse ends.

18. An apparatus for providing a visual or audible indicator as to whether a diamond is natural by measuring luminescence properties of the diamond, the apparatus comprising:
- a source of electromagnetic radiation;
- a light detection device for capturing visible light emitted by the diamond; and
- a control system configured:
  - to synchronize the source and light detection device;
  - to cause the source to irradiate the diamond with an excitation pulse of electromagnetic radiation; and
  - to cause the light detection device to capture visible light emitted by the diamond during at least one time window having a predetermined time relationship relative to the excitation pulse so as to obtain luminescence data;
- wherein the or each time window is chosen to encompass one or more specific markers in the luminescence properties of the diamond, said one or more markers characterized by luminescence decay time and luminescence wavelength and providing an indicator of whether the diamond is natural;

the apparatus further comprising:
- a processor configured to provide a visual or audible indicator as to whether the diamond is natural, or whether further analysis is required, based upon the presence or absence of the one or more specific markers.

19. The apparatus of claim 18, wherein the processor is further configured to indicate visually or audibly to a user that the diamond has passed or failed.

* * * * *